US 6,569,858 B2

(12) United States Patent
Prudhomme et al.

(10) Patent No.: US 6,569,858 B2
(45) Date of Patent: May 27, 2003

(54) 12,13-(PYRANOSYL)-INDOLO[2,3-A] PYRROLO[3,4-C]CARBAZOLE AND 12,13-(PYRANOSYL)-FURO[3,4-C]INDOLO[2,3-A] CARBAZOLES

(75) Inventors: Michelle Prudhomme, Clermont-Ferrand (FR); Pascale Moreau, Clermont-Ferrand (FR); Fabrice Anizon, Ennezat (FR); Christelle Marminon, Maison-Lafitte (FR); Ghanem Atassi, Saint-Cloud (FR); Alain Pierre, Les Alluets le Roi (FR); Bruno Pfeiffer, Saint Leu la Foret (FR); Pierre Renard, Le Chesnay (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/010,379

(22) Filed: Nov. 5, 2001

(65) Prior Publication Data

US 2002/0055510 A1 May 9, 2002

Related U.S. Application Data

(63) Continuation of application No. 09/714,746, filed on Nov. 16, 2000, now abandoned.

(30) Foreign Application Priority Data

Nov. 17, 1999 (FR) .............................. 99 14433

(51) Int. Cl.$^7$ .................. C07D 49/044; A61K 31/4985
(52) U.S. Cl. ....................... 514/250; 544/338
(58) Field of Search ................. 514/250; 544/338, 544/339, 340, 341

(56) References Cited

PUBLICATIONS

Anizon et al., Synthesis, biochemical and biological evaluation of staurosporine analogs from the microbial rebeccamycin. Bioorg. Med. Chem., 6, 1597–1604, 1998.*

* cited by examiner

Primary Examiner—John M. Ford
(74) Attorney, Agent, or Firm—The Firm of Hueschen and Sage

(57) ABSTRACT

A compound selected from those of formula (I):

wherein:

$R_1$ and $R_2$, which may be identical or different, represent a group of formula U-V wherein U represents single bond, or alkylene which is optionally substituted and/or unsaturated, and V is as defined in the description, G represents oxygen, or $NR_3$ wherein $R_3$ is as defined in the description, X represents hydrogen, hydroxy, alkoxy, mercapto or alkylthio, Y represents hydrogen, or X+Y represents carbonyl, $X_1$ represents hydrogen, hydroxy, alkoxy, mercapto or alkylthio, $Y_1$ represents hydrogen, or $X_1+Y_1$ represents carbonyl, $R_4$, $R_5$, and $R_6$ are as defined in the description, its isomers, and pharmaceutically-acceptable acid or base addition salts thereof, and medicinal products containing the same are useful in the treatment of cancer.

11 Claims, No Drawings

12,13-(PYRANOSYL)-INDOLO[2,3-A] PYRROLO[3,4-C]CARBAZOLE AND 12,13-(PYRANOSYL)-FURO[3,4-C]INDOLO[2,3-A] CARBAZOLES

The present application is a continuation of 09/714,746 of Nov. 16, 2000, now abandoned.

FIELD OF THE INVENTION

The present invention relates to new 12,13-(pyranosyl)-indolo[2,3-a]pyrrolo[3,4-c]-carbazole and 12,13-(pyranosyl)-furo[3,4-c]indolo[2,3-a]carbazole compounds, and to pharmaceutical compositions containing them.

Anti-cancer therapeutic requirements call for the constant development of new cytotoxic agents, with the aim of obtaining medicaments that are both more active and better tolerated. The compounds of the present invention have, for example, anti-tumour properties, which makes them useful in the treatment of cancers.

PRIOR ART OF THE INVENTION

Various chemical modifications have been made to the rebeccamycin or staurosporine structure with a view to improving the anti-tumour potential. Mention may be made, for example, of Patent Specifications WO 98/07433, WO 99/02532 and EP 602 597 which claim rebeccamycin compounds comprising structural modifications to the oside moiety of the molecule and to the substituents present in the hexacyclic system. The article published in <<Bioorganic and Medicinal Chemistry 1998, 6, 1597–1604>> also describes such compounds having good cytotoxic activity.

In addition to the fact that the compounds of the invention are new, they have a surprising in vitro and in vivo activity that is superior to that observed hitherto. The compounds discovered by the Applicant accordingly have anti-tumour properties that make them particularly useful in the treatment of cancers.

DETAIL DESCRIPTION OF THE INVENTION

More especially, the present invention relates to compounds of formula (I)

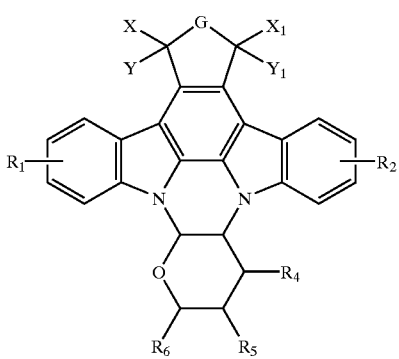

(I)

wherein:

$R_1$ and $R_2$ which may be identical or different, each independently of the other represents a group of formula U-V wherein:
U represents a single bond or a linear or branched ($C_1$–$C_6$)alkylene chain, optionally substituted by one or more identical or different groups selected from halogen and hydroxy, and/or optionally containing one or more unsaturated bonds, V represents a group selected from a hydrogen atom, a halogen atom, a cyano group, a nitro group, an azido group, a linear or branched ($C_1$–$C_6$)alkyl group, an aryl group, an aryl-($C_1$–$C_6$)alkyl group in which the alkyl moiety is linear or branched, a hydroxy group, a linear or branched ($C_1$–$C_6$)alkoxy group, an aryloxy group, an aryl-($C_1$–$C_6$)alkoxy group in which the alkoxy moiety is linear or branched, a formyl group, a carboxy group, an aminocarbonyl group, an NRaRb, —C(O)—$T_1$, —C(O)—NRa—$T_1$, —NRa—C(O)—$T_1$, —O—C(O)—$T_1$, —C(O)—O—$T_1$, —O—$T_2$—NRaRb, —O—$T_2$—ORa, —O—$T_2$—$CO_2$Ra, —NRa—$T_2$—NRaRb, —NRa—$T_2$—ORa, —NRa—$T_2$—$CO_2$Ra and an —S(O)$_n$—Ra group, wherein:
Ra and Rb, which may be identical or different, each represents a group selected from a hydrogen atom, a linear or branched ($C_1$–$C_6$)alkyl group, an aryl group and an aryl-($C_1$–$C_6$)alkyl group in which the alkyl moiety is linear or branched, or
Ra+Rb form together with the nitrogen atom carrying them a monocyclic heterocycle having from 5 to 7 ring members, optionally containing within the ring system a second hetero atom selected from oxygen and nitrogen, and optionally being substituted by a group selected from linear or branched ($C_1$–$C_6$)alkyl, hydroxy, linear or branched ($C_1$–$C_6$)alkoxy, amino, linear or branched ($C_1$–$C_6$)alkylamino and di-($C_1$–$C_6$) alkylamino in which each alkyl moiety is linear or branched,
$T_1$ represents a group selected from linear or branched ($C_1$–$C_6$)alkyl, aryl, aryl-($C_1$–$C_6$)alkyl in which the alkyl moiety is linear or branched, and a linear or branched ($C_1$–$C_6$)alkylene chain substituted by a group selected from —ORa, —NRaRb, —$CO_2$Ra, —C(O)Ra and —C(O)NRaRb wherein Ra and Rb are as defined hereinbefore,
$T_2$ represents a linear or branched ($C_1$–$C_6$)alkylene chain,
n represents an integer from 0 to 2 inclusive,
G represents an oxygen atom or an $NR_3$ group wherein $R_3$ represents a group selected from a hydrogen atom, a linear or branched ($C_1$–$C_6$)alkyl group, an aryl group, an aryl-($C_1$–$C_6$)alkyl group in which the alkyl moiety is linear or branched, a cycloalkyl group, a cycloalkyl-($C_1$–$C_6$)alkyl group in which the alkyl moiety is linear or branched, an —ORa group, an —NRaRb group, an —O—$T_2$—NRaRb group, an —NRa—$T_2$—NRaRb group, a ($C_1$–$C_6$) hydroxyalkylamino group in which the alkyl moiety is linear or branched, a di(($C_1$–$C_6$)hydroxyalkyl)amino group in which each alkyl moiety is linear or branched, a —C(O)—Ra group, an —NH—C(O)—Ra group and a linear or branched ($C_1$–$C_6$)alkylene chain substituted by one or more identical or different groups selected from halogen atoms and the groups cyano, nitro, —ORa, —NRaRb, —$CO_2$Ra, —C(O)Ra, ($C_1$–$C_6$) hydroxyalkylamino in which the alkyl moiety is linear or branched, di(($C_1$–$C_6$)hydroxyalkyl)amino in which each alkyl moiety is linear or branched, and —C(O)—NHRa, the groups Ra, Rb and $T_2$ being as defined hereinbefore,
X represents a group selected from a hydrogen atom, a hydroxy group, a linear or branched ($C_1$–$C_6$)alkoxy group, a mercapto group and a linear or branched ($C_1$–$C_6$) alkylthio group,
Y represents a hydrogen atom, or X and Y together with the carbon atom carrying them form a carbonyl group, $X_1$ represents a group selected from a hydrogen atom, a hydroxy group, a linear or branched ($C_1$–$C_6$)alkoxy group, a mercapto group and a linear or branched ($C_1$–$C_6$) alkylthio group.

$Y_1$ represents a hydrogen atom, or $X_1$ and $Y_1$ together with the carbon atom carrying them form a carbonyl group, $R_4$ and $R_5$, which may be identical or different, each independently of the other represents a group selected from a hydrogen atom, a halogen atom, a hydroxy group, a linear or branched ($C_1$–$C_6$)alkoxy group, an aryloxy group, an aryl-($C_1$–$C_6$)alkoxy group in which the alkoxy moiety is linear or branched, a linear or branched ($C_1$–$C_6$) alkyl group, an aryl-($C_1$–$C_6$)alkyl group in which the alkyl moiety is linear or branched, an aryl group, an amino group (itself being optionally substituted by one or two identical or different groups selected from linear or branched ($C_1$–$C_6$)alkyl, aryl and aryl-($C_1$–$C_6$)alkyl in which the alkyl moiety is linear or branched), an azido group, an —N=NRa group (wherein Ra is as defined hereinbefore), and an —O—C(O)—Rc group wherein Rc represents a linear or branched ($C_1$–$C_6$)alkyl group (optionally substituted by one or more groups selected from halogen, hydroxy, amino, linear or branched ($C_1$–$C_6$)alkylamino and di-($C_1$–$C_6$)alkylamino in which each alkyl moiety is linear or branched), an aryl group, an aryl-($C_1$–$C_6$)alkyl in which the alkyl moiety is linear or branched, a cycloalkyl group and a heterocycloalkyl group.

$R_6$ represents a group of formula —$U_1$–$R_4$ wherein $U_1$ represents a single bond or a methylene group, and $R_4$ is as defined hereinbefore, or $R_4$, $R_5$ and $R_6$ taken in pairs in adjacent or non-adjacent positions form with the carbon atoms carrying them a ring system having from 3 to 6 ring members, containing one or two oxygen atoms, with the remaining group $R_4$, $R_5$ or $R_6$ that does not belong to the ring system having any one of the definitions of $R_4$, $R_5$ or $R_6$ given hereinbefore, their isomers, and addition salts thereof with a pharmaceutically acceptable acid or base, provided that the compounds of formula (I) are other than the following compounds:

1,11-dichloro-12,13-[1,2-(4—O-methyl-β-D-mannopyranosyl)]-6,7,12,13-tetrahydro-(5H)-indolo[2,3-a]pyrrolo[3,4-c]carbazole-5,7-dione, 12,13-[1,2-(4—O-methyl-β-D-mannopyranosyl)-6,7,12,13-tetrahydro-(5H)-indolo[2,3-a]-pyrrolo[3,4-c]carbazole-5,7-dione, 12,13-[1,2-(4—O-methyl-β-D-mannopyranosyl)-6,7,12,13-tetrahydro-(5H)-indolo[2,3-a]-pyrrolo[3,4-c]carbazol-5-one, and 12,13-[1,2-(4—O-methyl-β-D-mannopyranosyl)-5,6,12,13-tetrahydro-(7H)-indolo[2,3-a]pyrrolo[3,4-c]-carbazol-7-one, it also being understood that:

"cycloalkyl" is understood to mean a monocyclic or bicyclic group that is saturated or unsaturated but without aromatic character, having from 3 to 10 carbon atoms, being optionally substituted by one or more identical or different groups selected from halogen, linear or branched ($C_1$–$C_6$) alkyl, linear or branched ($C_1$–$C_6$)trihaloalkyl, hydroxy, linear or branched ($C_1$–$C_6$)alkoxy, and amino optionally substituted by one or two linear or branched ($C_1$–$C_6$)alkyl groups, "heterocycloalkyl" is understood to mean a cycloalkyl group as defined above having within the ring system one or two identical or different hetero atoms selected from oxygen, nitrogen and sulphur, "aryl" is understood to mean a phenyl, naphthyl, dihydronaphthyl, tetrahydronaphthyl, indenyl or indanyl group, each of those groups being optionally substituted by one or more identical or different groups selected from halogen, linear or branched ($C_1$–$C_6$)alkyl, linear or branched ($C_1$–$C_6$)trihaloalkyl, hydroxy, linear or branched ($C_1$–$C_6$)alkoxy, and amino optionally substituted by one or two linear or branched ($C_1$–$C_6$)alkyl groups.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

Advantageously, the preferred group G according to the invention is the group $NR_3$ wherein $R_3$ is as defined for formula (I).

According to an advantageous embodiment of the invention, the preferred compounds are those wherein X and Y together with the carbon atom carrying them form a carbonyl group, and $X_1$ and $Y_1$ together with the carbon atom carrying them form a carbonyl group.

According to another advantageous embodiment, the preferred compounds of the invention are the compounds of formula (I bis)

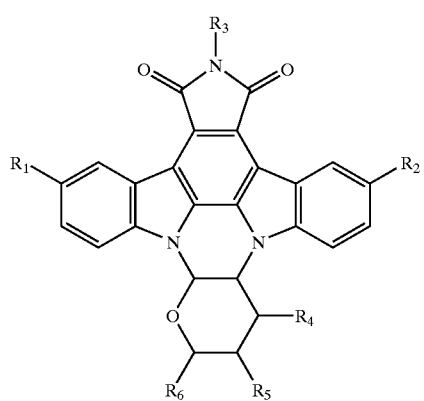

(Ibis)

wherein $R_1$, $R_2$, $R_3$, $R_4$, $R_5$ and $R_6$ are as defined for formula (I).

Preferably the substituents $R_1$ and $R_2$, which, according to the invention, may be identical or different, represent a group of formula U-V wherein U represents a single bond and V represents a group selected from a halogen atom, a hydrogen atom, a nitro group, a formyl group, a hydroxy group, and a linear or branched ($C_1$–$C_6$)alkylene chain substituted by a hydroxy group.

Especially advantageously the substituents $R_1$ and $R_2$ are identical.

The preferred substituents $R_3$ according to the invention are the hydrogen atom, the hydroxy group and the linear or branched ($C_1$–$C_6$)alkylene chain substituted by a group selected from NRaRb and ORa wherein Ra and Rb are as defined for formula (I).

According to a final especially advantageous embodiment, the preferred compounds of the invention are the compounds of formula (I ter):

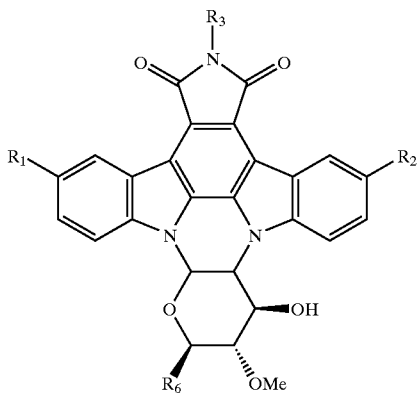

(I ter)

wherein $R_1$, $R_2$, $R_3$ and $R_6$ are as defined for formula (I).

The preferred compounds according to the invention are:

3,9-diformyl-12,13-[1,2-(4—O-methyl-β-D-mannopyranosyl)]-6,7,12,13-tetrahydro-(5H)-indolo[2,3-a]pyrrolo[3,4-c]carbazole-5,7-dione, 3,9-dinitro-12,13-[1,2-(4—O-methyl-β-D-mannopyranosyl)]-6,7,12,13-tetrahydro-(5H])-indolo[2,3)-a]pyrrolo[3,4-c]carbazole-5,7-dione, 3-nitro-12,13-[1,2-(4—O-methyl-β-D-mannopyranosyl)]-6,7,12,13-tetrahydro-(5H)-indolo[2,3-a]pyrrolo[3,4-c]carbazole-5,7-dione, 9-nitro-12,13-[1,2-(4—O-methyl-β-D-mannopyranosyl)]-6,7,12,13-tetrahydro-(5H)-indolo[2,3-a]pyrrolo[3,4-c]carbazole-5,7-dione, 6-hydroxy-12,13-[1,2-(4—O-methyl-β-D-mannopyranosyl)]-6,7,12,13-tetrahydro-(5H)-indolo[2,3-a]pyrrolo[3,4-c]carbazole-5,7-dione, 3,9-di-(hydroxymethyl)-12,13-[1,2-(4—O-methyl-β-D-mannopyranosyl)]-6,7,12,13-tetrahydro-(5H)-indolo[2,3-a]pyrrolo[3,4-c]carbazole-5,7-dione, 3,9-dinitro-12,13-[1,2-(3,6-anhydro-4—O-methyl-β-D-mannopyranosyl)]-6,7,12,13-tetrahydro-(5H)-indolo[2,3-a]pyrrolo[3,4-c]carbazole-5,7-dione, 3,9-dihydroxy-12,13-[1,2-(4—O-methyl-β-D-mannopyranosyl)]-6,7,12,13-tetrahydro-(5H)-indolo[2,3-a]pyrrolo[3,4-c]carbazole-5,7-dione, 3,9-dibromo-12,13-[1,2-(4—O-methyl-β-D-mannopyranosyl)]-6,7,12,13-tetrahydro-(5H)-indolo[2,3-a]pyrrolo[3,4-c]carbazole-5,7-dione, and 6-diethylaminoethyl-12,13-[1,2-(4—O-methyl-β-D-mannopyranosyl)]-6,7,12,13-tetrahydro-(5H)-indolo[2,3-a]pyrrolo[3,4-c]carbazole-5,7-dione and its hydrochloride.

The isomers and addition salts with a pharmaceutically acceptable acid or base of the preferred compounds of the invention form an integral part of the invention.

The present invention relates also to a process for the preparation of compounds of formula (I), characterised in that there is used as starting material a compound of formula (II):

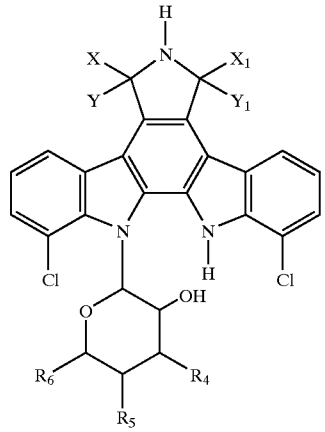

(II)

wherein X, Y, $X_1$, $Y_1$, $R_4$, $R_5$ and $R_6$ are as defined for formula (I),
which is treated in a basic medium with para-toluenesulphonic acid, to yield a compound of formula (III):

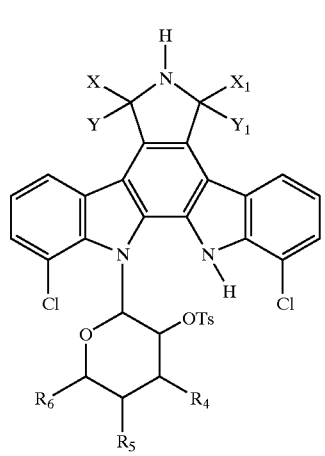

(III)

wherein X, Y, $X_1$, $Y_1$, $R_4$, $R_5$ and $R_6$ are as defined hereinbefore,
which compound of formula (III) is reacted with sodium azide, to yield principally a compound of formula (I/a), a particular case of the compounds of formula (I):

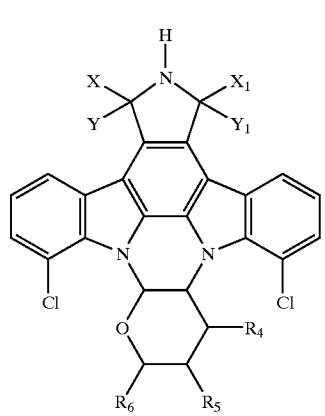

(I/a)

wherein X, Y, $X_1$, $Y_1$, $R_4$, $R_5$ and $R_6$ are as defined hereinbefore, which compound of formula (I/a) is subjected to conditions of hydrogenolysis, to yield a compound of formula (I/b), a particular case of the compounds of formula (I):

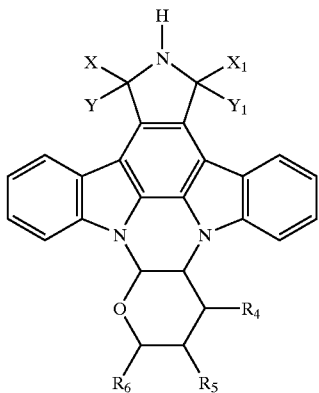

(I/b)

wherein X, Y, $X_1$, $Y_1$, $R_4$, $R_5$ and $R_6$ are as defined hereinbefore, which compound of formula (I/b) is treated with aqueous sodium hydroxide solution and then treated with hydrochloric acid to yield a compound of formula (I/c), a particular case of the compounds of formula (I):

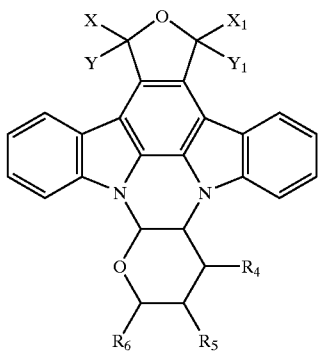

(I/c)

wherein X, Y, $X_1$, $Y_1$, $R_4$, $R_5$ and $R_6$ are as defined hereinbefore, which compound of formula (I/c) is subjected to the action of a compound of formula (IV):

$R_{3a}$—$NH_2$ (IV)

wherein $R_{3a}$ has the same definitions as $R_3$ with the exception of a hydrogen atom, to yield a compound of formula (I/d), a particular case of the compounds of formula (I):

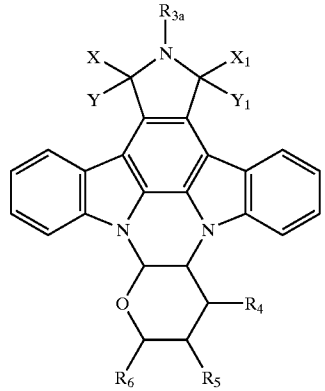

(I/d)

wherein X, Y, $X_1$, $Y_1$, $R_{3a}$, $R_4$, $R_5$ and $R_6$ are as defined hereinbefore,
the totality of the compounds of formulae (I/b) to (I/d) constituting the compounds of formula (I/e):

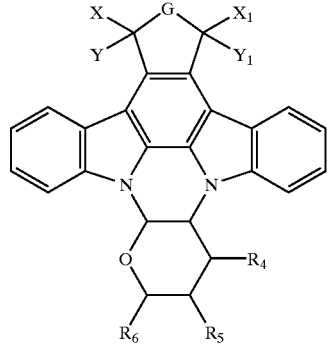

(I/e)

wherein G, X, Y, $X_1$, $Y_1$, $R_4$, $R_5$ and $R_6$ are as defined for formula (I), which compound of formula (I/e) is subjected to an electrophilic aromatic addition reaction or to a nucleophilic aromatic addition reaction, according to conventional conditions of organic synthesis well known to the person skilled in the art, to yield a compound of formula (I/f), a particular case of the compounds of formula (I):

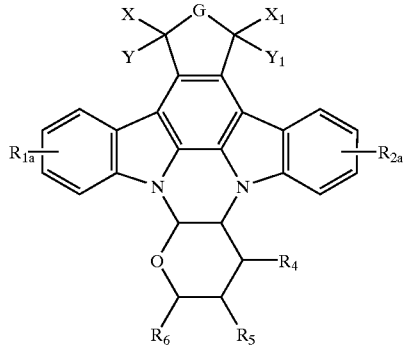

(I/f)

wherein G, X, Y, $X_1$, $Y_1$, $R_4$, $R_5$ and $R_6$ are as defined hereinbefore, and $R_{1a}$ and $R_{2a}$ have the same definitions as $R_1$ and $R_2$, respectively, except that $R_{1a}$ and $R_{2a}$ cannot simultaneously represent a hydrogen atom,
which compounds of formulae (I/a) to (I/f) constitute the totality of the compounds of formula (I), which are purified, if necessary, according to conventional purification techniques, which may, if desired, be separated into their different isomers according to a conventional separation technique, the substituents $R_4$, $R_5$ and $R_6$ of which are adjusted according to conventional methods of organic synthesis used in the field of sugar chemistry, and which are converted, if desired, to addition salts thereof with a pharmaceutically acceptable acid or base.

The compounds of formulae (II) and (IV) are either commercial compounds or are obtained according to conventional methods of organic synthesis readily accessible to the person skilled in the art.

The compounds of formula (I) have especially valuable anti-tumour properties. They have excellent in vitro cytotoxicity on cell lines, and an action on the cell cycle. The characteristic properties of the compounds enable them to be used therapeutically as anti-tumour agents.

The present invention relates also to pharmaceutical compositions comprising as active ingredient at least one compound of formula (I), an optical isomer thereof, or an addition salt thereof with a pharmaceutically acceptable acid or base, on its own or in combination with one or more inert, non-toxic, pharmaceutically acceptable excipients or carriers.

Among the pharmaceutical compositions according to the invention, there may be mentioned more especially those that are suitable for oral, parenteral (intravenous, intramuscular or subcutaneous), per- or trans-cutaneous, nasal, rectal, perlingual, ocular or respiratory administration, and especially tablets or dragees, sublingual tablets, gelatin capsules, capsules suppositories, creams, ointments, dermal gels, injectable or drinkable preparations, aerosols, eye or nose drops, etc.

Owing to the characteristic pharmacological properties of the compounds of formula (I), pharmaceutical compositions comprising the said compounds of formula (I) as active ingredient are accordingly especially useful in the treatment of cancers.

The useful dosage varies according to the age and weight of the patient, the route of administration, the nature and severity of the disorder, and whether any associated treatments are being taken, and ranges from 0.5 mg to 500 mg in one or more administrations per day.

The following Examples illustrate the invention but do not limit it in any way. The starting materials used are known products or are prepared according to known procedures.

The structures of the compounds described in the Examples were determined according to the usual spectrophotometric techniques (infrared, nuclear magnetic resonance, mass spectrometry, etc.).

EXAMPLE 1

1,11-Dichloro-12,13-[1,2-(4—O-methyl-β-D-mannopyranosyl)]-6,7,12,13-tetrahydro-(5H)-indolo[2,3-a]pyrrolo[3,4-c]carbazole-5,7-dione Step 1: 1,11-Dichloro-12-[4—O-methyl-2—O-tosyl-β-D-glucopyranosyl]-6,7,12,13-tetrahydro-(5H)-indolo[2,3-a]pyrrolo[3,4-c]carbazole-5,7-dione 1 equivalent of potassium carbonate and 1 equivalent of tosyl chloride are added to a solution of 1.7 mmol of rebeccamycin in 200 ml of tetrahydrofuran. After 48 hours' reflux and concentration under reduced pressure, chromatography of the residue over silica gel (cyclohexane/ethyl acetate 70/30) enables the expected product to be isolated.

Melting point: 168–170° C.

Step 2: 1,11-Dichloro-12,13-[1,2-(4—O-methyl-β-D-mannopyranosyl)]-6,7,12,13-tetrahydro-(5H)-indolo[2,3-a]pyrrolo[3,4-c]carbazole-5,7-dione 10 equivalents of sodium azide are added to a solution of 0.62 mmol of the compound obtained in Step 1 in 16 ml of dimethylformamide. After 6 hours at 70° C., and then cooling, the reaction mixture is hydrolysed, and extracted with ethyl acetate. The organic phase is then washed, dried, filtered and then concentrated under reduced pressure. Chromatography over silica gel (ethyl acetate/dichloromethane: 10/90) enables the expected product to be isolated.

Melting point: 296–298° C.

Mass spectrum (FAB$^+$): m/z calculated=551.0650 [M]$^+$ m/z found=551.0647 [M]$^+$

EXAMPLE 2

12,13-[1,2-(4—O-Methyl-β-D-mannopyranosyl)-6,7,12,13-tetrahydro-(5H)-indolo[2,3-a]pyrrolo[3,4-c]carbazole-5,7-dione A mixture of 0.855 mmol of the compound of Example 1, 0.57 g of 5% Pd/C and 0.57 g of ammonium formate in 200 ml of methanol is stirred at room temperature for 48 hours and then filtered over Celite. After concentration of the filtrate under reduced pressure, chromatography over silica gel (cyclohexane/ethyl acetate: 40/60) enables the expected product to be isolated.

Melting point: 284–286° C.

Mass spectrum (FAB$^+$): m/z calculated=484.1508 [M+H]$^+$ m/z found=484.1516 [M+H]$^+$

EXAMPLE 3

12,13-[1,2-(4—O-Methyl-β-D-mannopyranosyl)]-dihydrofuro[3,4-c]-indolo[2,3-a]carbazole-5,7-dione A solution of 0.414 mmol of the compound of Example 2, 420 mg of sodium hydroxide and 70 ml of water is refluxed for 3 hours. The mixture is then diluted, rendered acidic with an aqueous 1N hydrochloric acid solution and extracted with ethyl acetate. The organic phase is washed, dried, filtered and then concentrated under reduced pressure. Chromatography over silica gel (ethyl acetate/cyclohexane: 70/30) enables the expected product to be isolated.

Melting point: >300° C.

Mass spectrum (FAB$^+$): m/z calculated=485.1349 [M+H]$^+$ m/z found=485.1333 [M+H]$^+$

EXAMPLE 4

6-Methyl-12,13-[1,2-(4—O-methyl-β-D-mannopyranosyl)]-6,7,12,13-tetrahydro-(5H)-indolo[2,3-a]pyrrolo[3,4-c]carbazole-5,7-dione 0.118 mmol of the compound of Example 3 and a 2M solution of methylamine in 14 ml of tetrahydrofuran are stirred at 70° C. for 16 hours. After cooling, the reaction mixture is hydrolysed, causing the formation of a precipitate, which is purified by chromatography over silica gel (ethyl acetate/cyclohexane: 80/20), enabling the expected product to be isolated.

Melting point: >300° C.

Mass spectrum (FAB$^+$): m/z calculated=497.1587 (M)$^+$ m/z found=497.1591 (M)$^+$

EXAMPLE 5

6-Hydroxy-12,13-[1,2-(4—O-methyl-β-D-mannopyranosyl)]-6,7,12,13-tetrahydro-(5H)-indolo[2,3-a]pyrrolo[3,4-c]carbazole-5,7-dione 14.4 mmol of hydroxylamine hydrochloride and 14.4 mmol of triethylamine are added to a solution of 0.207 mmol of the compound of Example 3 in 5 ml of dimethylformamide. After 23 hours at 70° C., an aqueous 1N hydrochloric acid solution, ethyl acetate and tetrahydrofuran are added. The organic phase is then washed, dried, filtered and then concentrated under reduced pressure. Chromatography over silica gel (tetrahydrofuran/methanol: 95/5) enables the expected product to be isolated.

Melting point: >260° C. (decomposition)

EXAMPLE 6

3,9-Diformyl-12,13-[1,2-(3,6-di-O-acetyl-4—O-methyl-β-D-mannopyranosyl)]-6,7,12,13-tetrahydro-(5H)-indolo[2,3-a]pyrrolo[3,4-c]carbazole-5,7-dione 0.2 ml of acetic anhydride is added to a solution, cooled to 0° C., of 0.207 mmol of the compound of Example 2 in 2 ml of pyridine. The reaction mixture is then stirred at room temperature for 18 hours. After hydrolysis and extraction with ethyl acetate, the organic phase is washed dried, filtered and then evaporated. The resulting residue is then diluted in 4 ml of dichloromethane, and 4.2 mmol of dichloromethyl methyl ether are added. After cooling to 0° C., 4.2 ml of a 1M solution of $TiCl_4$ in dichloromethane are added. The reaction mixture is then stirred for 24 hours at room temperature and then hydrolysed and extracted with ethyl acetate. The organic phase is dried, filtered and then evaporated. Chromatography of the residue over silica gel (cyclohexane/ethyl acetate: 1/1) enables the expected product to be isolated.

Infrared (KBr): $v_{C=O}$=1690, 1720 and 1755 $cm^{-1}$ $v_{NH,OH}$=3100–3600 $cm^{-1}$ Melting point: >200° C.

EXAMPLE 7

3,9-Diformyl-12,13-[1,2-(4—O-methyl-β-D-mannopyranosyl)]-6,7,12,13-tetrahydro-(5H)-indolo[2,3-a]pyrrolo[3,4-c]carbazole-5,7-dione 5 ml of an aqueous 28% ammonium hydroxide solution are added to a solution of 0.074 mmol of the compound of Example 6 in 10 ml of tetrahydrofuran and 5 ml of methanol. After 30 hours' reaction at 25° C., the mixture is concentrated. The residue is taken up in dichloromethane and washed with water. The organic phase is evaporated and the resulting residue is washed with acetone, enabling the expected product to be isolated.

Melting point: >300° C.

Infrared (KBr): $v_{C=O}$=1680,1710 and 1750 $cm^{-1}$ $v_{NH,OH}$=3100–3650 $cm^{-1}$

EXAMPLE 8

3,9-Di(hydroxymethyl)-12,13-[1,2-(3,6-di-O-acetyl-4—O-methyl-β-D-mannopyranosyl)]-6,7,12,13-tetrahydro-(5H)-indolo[2,3-a]pyrrolo[3,4-c]carbazole-5,7-dione A solution of 0.116 mmol of the compound of Example 6, 60 ml of methanol and 101 mg of Raney nickel is hydrogenated at 25° C. for 2 days, and then 0.591 g of Raney nickel (50% by weight in water) is added and the hydrogenation is maintained for 5 days. The reaction mixture is then filtered over Celite. After concentration of the filtrate under reduced pressure, chromatography over silica gel (ethyl acetate/cyclohexane: 90/10) enables the expected product to be isolated.

Melting point: >180° C. (decomposition)

Infrared (Br) $v_{C=O}$=1720, 1750 $cm^{-1}$ $v_{NH,OH}$=3150–3650 $cm^{-1}$

EXAMPLE 9

3,9-Di-(hydroxymethyl)-12,13-[1,2-(4—O-methyl-β-D-mannopyranosyl)]-6,7,12,13-tetrahydro-(5H)-indolo[2,3-a]pyrrolo[3,4-c]carbazole-5,7-dione The procedure is as for Example 7 using the compound of Example 8 as substrate.

Melting point: >300° C.

Infrared (KBr): $v_{C=O}$=1710, 1750 $cm^{-1}$ $v_{NH,OH}$=3100–3600 $cm^{-1}$

EXAMPLE 10

12,13-[1,2-(6-Chloro-6-deoxy-4—O-methyl-β-D-mannopyranosyl)]-6,7,12,13-tetrahydro-(5H)-indolo[2,3-a]pyrrolo[3,4-c]carbazole-5,7-dione 4 equivalents of $PPh_3$ and 2 equivalents of $CCl_4$ are added to a solution of 0.447 mmol of the compound of Example 2 in 2 ml of pyridine. After 3 hours' stirring at 25° C., the reaction mixture is poured into an aqueous 1N hydrochloric acid solution and then extracted with ethyl acetate. The organic phase is washed, dried, filtered and then concentrated under reduced pressure. Chromatography over silica gel enables the expected product to be isolated.

Melting point: >280° C. (decomposition)

Infrared (KBr): $v_{C=O}$=1710, 1750 $cm^{-1}$ $v_{NH,OH}$=3150–3600 $cm^{-1}$

EXAMPLE 11

12,13-[1,2-(3,6-Anhydro-4—O-methyl-β-D-mannopyranosyl)]-6,7,12,13-tetrahydro-(5H)-indolo[2,3-a]pyrrolo[3,4-c]carbazole-5,7-dione The product is isolated during the chromatography carried out in Example 10.

Melting point: >300° C.

Infrared (KBr): $v_{C=O}$=1720, 1750 $cm^{-1}$ $v_{NH,OH}$=3100–3600 $cm^{-1}$

EXAMPLE 12

12,13-[1,2-(6-Azido-6-deoxy-4—O-methyl-β-D-mannopyranosyl)]-6,7,12,13-tetrahydro-(5H)-indolo[2,3-a]pyrrolo[3,4-c]carbazole-5,7-dione A solution of 0.1 mmol of the compound of Example 10 in 1 ml of dimethylformamide, and 10 equivalents of sodium azide is stirred at 80° C. After 48 hours, the reaction mixture is taken up in ethyl acetate and washed with water. The organic phase is dried, filtered and evaporated. Chromatography over silica gel (dichloromethane/ethyl acetate 95/5) enables the expected product to be isolated.

Melting point: >250° C. (decomposition)

Infrared (KBr): $vC=O$=1700, 1750 $cm^{-1}$ $v_{N=N}$=2100 $cm^{-1}$ $v_{NH,OH}$=3150–3600 $cm^{-1}$

EXAMPLE 13

3,9-Dinitro-12,13-[1,2-(4—O-methyl-β-D-mannopyranosyl)]-6,7,12,13-tetrahydro-(5,H)-indolo[2,3-a]pyrrolo[3,4-c]carbazole-5,7-dione 10 equivalents of acetic anhydride are added at 0° C. to a solution of 0.5 mmol of the compound of Example 2 in 4.8 ml of pyridine. After 1 day's reaction at 25° C., the reaction mixture is hydrolysed, and then extracted with ethyl acetate. The organic phase is then washed, dried, filtered and evaporated. The resulting residue is diluted in 10 ml of tetrahydrofuran, and 5.6 ml of fuming nitric acid are added. After 5 days at 40° C., 2.8 ml of fuming nitric acid are added, and the mixture is maintained at 40° C. for 30 hours, and then hydrolysed. After extraction with ethyl acetate, the organic phase is washed, dried, filtered and then concentated under reduced pressure. The residue is then subjected to the process described in Example 8, enabling the expected product to be isolated.

Melting point: >300° C.

Infrared (KBr): $\nu_{C=O}$=1690, 1740 cm$^{-1}$ $\nu_{NH,OH}$=3170–3640 cm$^{-1}$

EXAMPLE 14

3- and 9-Nitro-12,13-[1,2-(4—O-methyl-β-D-mannopyranosyl)]-6,7,12,13-tetrahydro-(5H)-indolo[2,3-a]pyrrolo[3,4-c]carbazole-5,7-dione The procedure is as for Example 13 using concentrated nitric acid as reagent and carrying out the reaction at room temperature. Chromatography enables a mixture (1.5/1) of the 3-nitro and 9-nitro compounds to be isolated.

Melting point of the mixture: 293° C.

EXAMPLE 15

3,9-Diamino-12,13-[1,2-(4—O-methyl-β-D-mannopyranosyl)]-6,7,12,13-tetrahydro-(5H)-indolo[2,3-a]pyrrolo[3,4-c]carbazole-5,7-dione A solution of 0.094 mmol of the compound of Example 13 in 13 ml of tetrahydrofuran and 1.88 mmol of SnCl$_2$ is refluxed for 63 hours. After cooling, the reaction mixture is hydrolysed and the resulting precipitate is filtered off. The filtrate is adjusted to pH 10. After extraction with ethyl acetate, the organic phase is dried, filtered and evaporated, enabling the expected product to be isolated.

Melting point: >155° C. (decomposition)

Infrared (KBr): $\nu$C=O=1700, 1710, 1750 cm$^{-1}$ $\nu_{NH,OH,NH_2}$=3000–3600 cm$^{-1}$

EXAMPLE 16

3,9-Dinitro-12,13-[1,2-(3,6-anhydro-4—O-methyl-β-D-mannopyranosyl)]-6,7,12,13-tetrahydro-(5H)-indolo[2,3-a]-pyrrolo[3,4-c]carbazole-5,7-dione The procedure is as for Example 13 using the compound of Example 11 as substrate.

Melting point: >300° C.

Infrared (KBr): $\nu_{C=O}$=1720, 1760 cm$^{-1}$ $\nu_{NH}$=3100–3500 cm$^{-3}$

EXAMPLE 17

3-Nitro-12,13-[1,2-(3,6-anhydro-4—O-methyl-β-D-mannopyranosyl)]-6,7,12,13-tetrahydro-(5H)-indolo[2,3-a]-pyrrolo[3,4-c]carbazole-5,7-dione The product is isolated during synthesis of the compound of Example 16.

Melting point: >300° C.

Infrared (KBr): $\nu_{C=O}$=1710, 1750 cm$^{-1}$ $\nu_{NH}$=3200 cm$^{-1}$

EXAMPLE 18

3,9-Dihydroxy-12,13-[1,2-(4—O-methyl-β-D-mannopyranosyl)]-6,7,12,13-tetrahydro-(5H)-indolo[2,3-a]pyrrolo[3,4-c]carbazole-5,7-dione 37 μl of an aqueous 50% H$_2$O$_2$ solution and then 11 μl of an aqueous 95% sulphuric acid solution are added to a solution of 0.211 mmol of the compound of Example 6 in 6 ml of methanol. After 72 hours' stirring at room temperature, the reaction mixture is hydrolysed and then extracted with ethyl acetate. The organic phase is washed, dried, filtered and then evaporated. Chromatography over silica gel (toluene/tetrahydrofuran: 65/35) enables the expected product to be isolated.

Melting point: >258° C. (decomposition)

EXAMPLE 19

3,9-Dibromo-12,13-[1,2-(4—O-methyl-β-D-mannopyranosyl)]-6,7,12,13-tetrahydro-(5H)-indolo[2,3-a]pyrrolo[3,4-c]carbazole-5,7-dione A solution of 2.07 mmol of N-bromosuccinimide in 30 ml of tetrahydrofuran is added dropwise to a solution, cooled to 0° C., of 0.207 mmol of the compound of Example 2 in 20 ml of tetrahydrofuran. After 7 days' reaction at room temperature, the mixture is hydrolysed and extracted with ethyl acetate. The organic phase is dried, filtered and then concentrated under reduced pressure. Chromatography over silica gel (ethyl acetate/cyclohexane: 70/30) enables the expected product to be isolated.

Melting point: >300° C.

Infrared (KBr) $\nu_{C=O}$=1710, 1760 cm$^{-1}$ $\nu_{NH,OH}$=2700–3300 cm$^{-1}$

EXAMPLE 20

12,13-[1,2-(3—O-Bromoacetyl-4—O-methyl-β-D-mannopyranosyl)]-6,7,12,13-tetrahydro-(5H)-indolo[2,3-a]pyrrolo[3,4-c]carbazole-5,7-dione 79 mg of potassium tert-butylate and then, after 30 minutes at room temperature, 0.70 mmol of bromoacetyl bromide are added to a solution of 0.70 mmol of the compound of Example 2 in 12 ml of tetrahydrofuran. After 24 hours' reaction, the reaction mixture is hydrolysed and then extracted with ethyl acetate. The organic phase is dried, filtered and concentrated under reduced pressure. Chromatography over silica gel (dichloromethane/ethyl acetate: 70/30) enables the expected product to be isolated.

EXAMPLE 21

12,13-[1,2-(6—O-Bromoacetyl-4—O-methyl-β-D-mannopyranosyl)]-6,7,12,13-tetrahydro-(5H)-indolo[2,3-a]pyrrolo[3,4-c]carbazole-5,7-dione The procedure is as for Example 20 using potassium carbonate as base and carrying out the reaction at reflux of the tetrahydrofuran.

EXAMPLE 22

1,11-Dichloro-12,13-[1,2-(6-chloro-6-deoxy-4—O-methyl-β-D-mannopyranosyl)]-6,7,12,13-tetrahydro-(5H)-indolo[2,3-a]-pyrrolo[3,4-c]carbazole-5,7-dione The procedure is as for Example 10 using the compound of Example 1 as substrate.

EXAMPLE 23

12,13-[1,2-(6-Amino-6-deoxy-4—O-methyl-β-D-mannopyranosyl)]-6,7,12,13-tetrahydro-(5H)-indolo[2,3-a]-pyrrolo[3,4-c]carbazole-5,7-dione hydrochloride 7 mg of 10% Pd/C are added to a suspension of 0.126 mmol of the compound of Example 12 in 15 ml of methanol and 14 ml of ethyl acetate. The mixture is hydrogenated under a pressure of one atmosphere for 40 hours, and then filtered over Celite and washed successively by methanol, tetrahydrofuran and ethyl acetate. The filtrate is concentrated under reduced pressure and the resulting residue is suspended in 0.3 ml of methanol in the presence of 0.23 ml of a 1N hydrochloric acid solution. After stirring and addition of dichloromethane, the precipitate that forms is filtered off, enabling the expected product to be isolated.

Melting point: >300° C.

Infrared (KBr): $v_{C=O}$=1710, 1760 cm$^{-1}$ $v_{NH,OH}$=3270–3600 cm$^{-1}$

EXAMPLE 24

12,13-[1,2-(6-Iodo-6-deoxy-4—O-methyl-β-D-mannopyranosyl)]-6,7,12,13-tetrahydro-(5H)-indolo[2,3-a]pyrrolo[3,4-c]carbazole-5,7-dione 31 mmol of sodium iodide are added to a solution of 1.55 mmol of the compound of Example 10 in 80 ml of acetone. The mixture is stirred at reflux for 7 days and then the Rio solvent is removed by evaporation. The residue is taken up in ethyl acetate and then washed. The organic phase is dried, filtered and concentrated under reduced pressure. Chromatography over silica gel (cyclohexane/ethyl acetate: 60/40) enables the expected product to be isolated.

EXAMPLE 25

12,13-[1,2-(6-Dimethylamino-6-deoxy-4—O-methyl-β-D-mannopyranosyl)]-6,7,12,13-tetrahydro-(5H)-indolo[2,3-a]-pyrrolo[3,4-c]carbazole-5,7-dione hydrochloride 0.154 mmol of the compound of Example 24 is added to a solution of 3.14 mmol of dimethylamine in 5 ml of tetrahydrofuran. After stirring at room temperature for 2 days, the reaction mixture is hydrolysed and extracted with ethyl acetate. The organic phase is dried, filtered and concentrated under reduced pressure. The residue is diluted in 0.3 ml of methanol, and an aqueous 1N hydrochloric acid solution is added. After stirring and addition of dichloromethane, the precipitate that forms is filtered off, enabling the expected product to be isolated.

EXAMPLE 26

6-Amino-12,13-[1,2-(4—O-methyl-β-D-mannopyranosyl)]-6,7,12,13-tetrahydro-(5H)-indolo[2,3-a]pyrrolo[3,4-c]carbazole-5,7-dione 14 mmol of hydrazine hydrate are added to 0.20 mmol of the compound of Example 2. After 1.5 hours' stirring at 50° C., the reaction mixture is poured onto ice, and then extracted with ethyl acetate. The organic phase is then washed, dried, filtered and then concentrated under reduced pressure. Chromatography over silica gel (ethyl acetate/cyclohexane) enables the expected product to be isolated.

EXAMPLE 27

6-Formamido-12,13-[1,2-(4—O-methyl-β-D-mannopyranosyl)]-6,7,-12,13-tetrahydroindolo[2,3-a]pyrrolo[3,4-c]carbazole-5,7-dione 10 equivalents of formic hydrazide are added to a solution of 0.30 mmol of the compound of Example 3 in 10 ml of dimethylformamide. After stirring for 1 hour at 140° C., the reaction mixture is cooled and then hydrolysed, causing the formation of a precipitate, no which is filtered off and washed with water and then with ether, enabling the expected product to be isolated.

EXAMPLE 28

6-(2-Hydroxyethyl)-12,13-[1,2-(4—O-methyl-β-D-mannopyranosyl)]-6,7,12,13-tetrahydro-(5H)-indolo[2,3-a]pyrrolo[3,4-c]carbazole-5,7-dione A solution of 0.30 mmol of the compound of Example 3 and 1.3 ml of ethanolamine is stirred for 1 hour at room temperature, and then poured onto ice and extracted with ethyl acetate. The organic phase is dried, filtered and then concentrated under reduced pressure. Chromatography over silica gel (ethyl acetate/cyclohexane) enables the expected product to be isolated.

EXAMPLE 29

6-Diethylaminoethyl-12,13-[1,2-(4—O-methyl-β-D-mannopyranosyl)]-6,7,12,13-tetrahydro-(5H)-indolo[2,3-a]pyrrolo[3,4-c]carbazole-5,7-dione and its hydrochloride 26 µl of N,N-diethylethylenediamine are added dropwise to a solution of 58.5 mg of the compound of Example 3 dissolved in 7 ml of anhydrous tetrahydrofuran. The mixture is heated at 65° C. for 4 days away from light and is then cooled and taken up in a mixture (aqueous 1N hydrochloric acid solution/ethyl acetate). After extraction with ethyl acetate, the organic phase is dried, filtered and then concentrated under reduced pressure. The resulting residue is cooled to 0° C. and dissolved in 200 µl of methanol, and an aqueous 1.14N hydrochloric acid solution (108 µl) is added dropwise thereto. The mixture is stirred and then cyclohexane is added. The precipitate is filtered through a frit, enabling the expected product to be isolated.

Melting point: 250° C.

Infrared (KBr): $v_{C=O}$=1700, 1750 cm$^{-1}$ $v_{NH,OH}$=3200–3600 cm$^{-1}$

EXAMPLE 30

12,13-[1,2-(3,6-Di-O-acetyl-4—O-methyl-β-D-mannopyranosyl)]-6,7,-12,13-tetrahydro-(5H)-indolo[2,3-a]pyrrolo[3,4-c]carbazole-5,7-dione 0.68 ml of acetic anhydride is added dropwise to a solution of 351 mg of the compound of Example 2 in 7 ml of pyridine. The reaction mixture is stirred for 19 hours at room temperature. After hydrolysis, the organic product is extracted with ethyl acetate and then the organic phase is washed and dried. After removal of the solvent by evaporation, the residue is purified by chromatography over silica gel (cyclohexane/ethyl acetate: 3/2), enabling the expected product to be isolated.

Melting point: 106° C.

Infrared (KBr) $v_{C=O}$=1720, 1750 cm$^{-1}$ $v_{NH,OH}$=3100–3600 cm$^{-1}$

EXAMPLE 31

12,13-[1,2-(3—O-Acetyl-4—O-methyl-β-D-mannopyranosyl)]-6,7,12,13-tetrahydro-(5H)-indolo[2,3-a]pyrrolo[3,4-c]carbazole-5,7-dione 0.92 ml of boron trifluoride etherate is added dropwise to a solution, cooled to 0° C., of 337 mg of the compound of Example 30 dissolved in 30 ml of acetonitrile and 3 ml of water. After 24 hours at room temperature, 3 ml of water and 0.92 ml of boron trifluoride etherate are added. After a further 24 hours at room temperature, the reaction mixture is hydrolysed with an aqueous saturated sodium hydrogen carbonate solution. The organic product is extracted with ethyl acetate and then the organic phases are combined, washed and dried. After removal of the solvent by evaporation, chromatography over silica gel (cyclohexane/ethyl acetate: 1/1) enables the expected product to be isolated.

Melting point: 294° C.

Infrared (KBr): $v_{C=O}$=1720, 1750 cm$^{-1}$ $v_{NH,OH}$=3100–3600 cm$^{-1}$

EXAMPLE 32

12,13-[1,2-(3—O-Acetyl-6-deoxy-6-chloro-4—O-methyl-β-D-mannopyranosyl)]-6,7,12,13-tetrahydro-(5H)-indolo[2,3-a]pyrrolo[3,4-c]-carbazole-5,7-dione 154 mg of triphenylphosphine and then, dropwise, carbon tetrachloride (43 μl) are added in succession to a solution of 77 mg of the compound of Example 31 in 1.7 ml of pyridine. The reaction mixture is stirred at 40° C. for 65 hours, cooled and then poured into water (30 ml). The organic product is extracted with ethyl acetate, washed and then dried over magnesium sulphate. After removal of the solvent by evaporation, the residue is purified by chromatography over silica gel (cyclohexane/ethyl acetate: 55/45), enabling the expected product to be isolated.

Melting point: >300° C.

Infrared (KBr): $v_{C=O}$=1700, 1730, 1770 cm$^{-1}$ $v_{NH}$=3100–3600 cm$^{-1}$

EXAMPLE 33

3,9-Dinitro-12,13-[1,2-(3—O-acetyl-6-deoxy-6-chloro-4—O-methyl-β-D-mannopyranosyl)]-6,7,12,13-tetrahydro-(5H)-indolo[2,3-a]pyrrolo[3,4-c]carbazole-5,7-dione 3.5 ml of fuming nitric acid are added dropwise to a solution, cooled to 0° C., of 50.6 mg of the compound of Example 32 dissolved in 5 ml of anhydrous tetrahydrofuran. After 2 hours, the mixture is returned to room temperature and stirred for 21 hours. After hydrolysis, the organic product is extracted with ethyl acetate. The organic phases are combined, washed and dried over magnesium sulphate, and the solvent is removed by evaporation. Chromatography over silica gel (toluene/tetrahydrofuran: 7/3) yields the expected dinitro product.

EXAMPLE 34

3,9-Dinitro-12,13-[1,2-(6-deoxy-6-chloro-4—O-methyl-β-D-mannopyranosyl)]-6,7,12,13-tetrahydro-(5H)-indolo[2,3-a]pyrrolo[3,4c]-carbazole-5,7-dione Boron trifluoride etherate (48 μl) is added dropwise to a solution, cooled to 0° C., of 22.3 mg of the compound of Example 33 dissolved in 3 ml of acetonitrile, 0.3 ml of water and 2 ml of tetrahydrofuran. After 48 hours at 40° C., 0.3 ml of water and 1 ml of boron trifluoride etherate are added. After a further 24 hours at 40° C., the same proportions of water and boron trifluoride etherate are added. After 24 hours at room temperature, the reaction mixture is hydrolysed with an aqueous saturated sodium hydrogen carbonate solution. The organic product is extracted with ethyl acetate and then the organic phases are combined, washed and dried over magnesium sulphate. After removal of the solvent by evaporation, chromatography over silica gel (toluene/tetrahydrofuran: 1/1) and then (cyclohexane/acetone 2/3) enables the expected product to be isolated.

EXAMPLE 35

3,9-Dinitro-12,13-[1,2-(6-azido-6-deoxy-4—O-methyl-β-D-mannopyranosyl)]-6,7,12,13-tetrahydro-(5H)-indolo[2,3-a]pyrrolo[3,4-c]-carbazole-5,7-dione The procedure is as for Example 10 using the compound of Example 34 as starting material.

Melting Point: >300° C.

Infrared (KBr): $v_{C=O}$=1720, 1760 cm$^{-1}$ $v_{NH}$=3200–3600 cm$^{-1}$ $v_{N3}$=2100 cm$^{-1}$

EXAMPLE 36

3,9-Dimethoxycarbonyl-12,13-[1,2-(4—O-methyl-β-D-mannopyranosyl)]-6,7,12,13-tetrahydro-(5H)-indolo[2,3-a]pyrrolo[3,4-c]carbazole-5,7-dione A mixture of 290 mg of the compound of Example 2 and 6 ml of pyridine is cooled to 0° C. and then 0.6 ml of acetic anhydride is added. The reaction mixture is stirred at room temperature for 18 hours. Water is added and the mixture is stirred for 40 minutes, and then extracted with ethyl acetate. The organic phase is washed and then dried over MgSO$_4$. The solvent is removed by evaporation and the residue is dissolved in 9 ml of dichloromethane. Dichloromethyl methyl ether (1.08 ml) is added and the mixture is cooled to 0° C. before the addition of a 1M solution of TiCl$_4$ in 11.96 ml of dichloromethane. The mixture is stirred at room temperature for 24 hours and then hydrolysed with water. The reaction mixture is stirred for one hour and then extracted with ethyl acetate. The organic phase is dried over MgSO$_4$ and the solvent is removed by evaporation. The residue is then dissolved in 6 ml of methanol before the addition of a 50% solution in water of hydrogen peroxide (0.4 ml) and then the addition of 95% sulphuric acid (1.6 ml). The mixture is stirred for 72 hours at room temperature. After 30 minutes' hydrolysis, the reaction mixture is extracted with ethyl acetate. The organic phases are combined, dried over magnesium sulphate and filtered, and the solvent is removed by evaporation. The resulting residue is then dissolved in 22 ml of methanol before the dropwise addition of an aqueous 28% ammonium hydroxide solution (10 ml). The mixture is stirred at room temperature for 24 hours. After removal of the solvents by evaporation, the residue is taken up in a mixture of water/ethyl acetate. The reaction mixture is extracted with ethyl acetate. The organic phases are combined, washed with an aqueous sodium chloride solution, dried over magnesium sulphate and filtered, and the solvent is removed by evaporation. The residue is purified by chromatography over silica gel (cyclohexane/acetone: 1/1) to yield the expected product.

EXAMPLE 37

N$^3$,N$^9$-Bis(3-aminopropyl)-5,7-dioxo-12,13-[1,2-(4—O-methyl-β-D-mannopyranosyl)]-6,7,12,13-tetrahydro-(5,H)-indolo[2,3-a]pyrrolo[3,4-c]carbazole-3,9-dicarboxamide 0.2 ml of 1,3-diaminopropane is added to a solution of 1.26 ml of 2N Al(CH$_3$)$_3$ in hexane at −20° C. The mixture is stirred at −20° C. for 20 minutes and is then slowly returned to room temperature. 1.36 g of the compound of Example 7 dissolved in 15 ml of dichloromethane is added, and the solution is heated at reflux for 24 hours. The reaction mixture is hydrolysed with a solution of 4 ml of 0.7M hydrochloric acid. After stirring for 30 minutes, the aqueous phase is separated off and extracted with ethyl acetate. The organic phase is washed and then dried. After removal of the solvent by evaporation, the resulting residue is purified by chromatography over a silica column to yield the expected product.

EXAMPLE 38

3,9-Dichloro-12,13-[1,2-(4—O-methyl-β-D-mannopyranosyl)]-6,7,12,-13-tetrahydro-(5H)-indolo[2,3-a]pyrrolo[3,4-c]carbazole-5,7-dione A solution of 166 mg of N-chlorosuccinimide dissolved in 6 ml of tetrahydrofuran is added dropwise to a solution, cooled to 0° C., of 60 mg of the compound of Example 2 in 3 ml of tetrahydrofuran. The mixture is stirred for 4 days at room temperature. After 10 minutes' hydrolysis with 50 ml of water, the dichloro compound is extracted with ethyl acetate. The organic phase is dried and filtered, and the solvent is removed by evaporation. The residue is purified by chromatography over silica gel (cyclohexane/ethyl acetate: 3/7) to yield the expected product.

EXAMPLE 39

3,9-Diamino-12,13-[1,2-(4—O-methyl-β-D-mannopyranosyl)]-6,7,12,-13-tetrahydro-5-oxo-(5H)-indolo[2,3-a]pyrrolo[3,4-c]carbazole and 3,9-diamino-12,13-[1,2-(4—O-methyl-β-D-mannopyranosyl)]-6,7,12,13-tetrahydro-7-oxo-(5H)-indolo[2,3-a]pyrrolo[3,4-c]carbazole 1 g of zinc amalgam is added to a solution of 106 mg of the compound of Example 15 in 14 ml of ethanol in the presence of 2.3 ml of 6N hydrochloric acid. The mixture is refluxed for 4 hours and then filtered. The solid residue is washed with ethyl acetate. The filtrate is evaporated, and the residue is taken up in ethyl acetate, and washed with an aqueous saturated $NaHCO_3$ solution, and then with water. The organic phase is dried over $MgSO_4$. The solvent is removed by evaporation and the residue is purified by chromatography over a silica column (ethyl acetate/methanol: 9/1), enabling a mixture of the expected regioisomers to be isolated.

EXAMPLE 40

12,13-[1,2-(3—O-Lysine-4—O-methyl-β-D-mannopyranosyl)]-6,7,12,13-tetrahydro-(5H)-indolo[2,3-a]pyrrolo[3,4-c]carbazole-5,7-dione and its Hydrochloride 68 mg of hydroxybenzotriazole and 114 mg of dicyclohexylcarbodiimide are added to a solution, cooled to 0° C., of 10 ml of di-tert-butoxycarbonyl-lysine in dimethylformamide. The mixture is stirred at room temperature for 30 minutes before being added to a suspension of 242 mg of the compound of Example 2 in 5 ml of tetrahydrofuran, that solution being previously stirred at room temperature in the presence of 69 mg of potassium carbonate. The reaction mixture so obtained is heated at 50° C. for 24 hours before being hydrolysed with a saturated NaCl solution, and then extracted with ethyl acetate. The combined organic phases are dried and then filtered and concentrated under reduced pressure. Chromatography of the residue over silica gel (cyclohexane/ethyl acetate: 3/7) enables a compound to be isolated, which is then dissolved in a mixture of 3M HCl in 2.5 ml of ethyl acetate. After 5 hours' stirring at room temperature, the reaction mixture is evaporated to yield crystals which are washed with ethyl acetate to yield the expected product in the form of its hydrochloride.

Pharmacological Study of the Compounds of the Invention

EXAMPLE 41

In vitro Activity

Murine Leukaemia L1210

The murine leukaemia L1210 was used in vitro. The cells are cultured in complete RPMI 1640 culture medium comprising 10% foetal calf serum, 2 mM glutamine, 50 units/ml of penicillin, 50 μg/ml of streptomycin and 10 mM Hepes, pH 7.4. The cells are distributed on microplates and are exposed to the cytotoxic compounds for four doubling periods, that is to say 48 hours. The number of viable cells is then quantified by a colorimetric assay, the Microculture Tetrazolium Assay (J. Carmichael et al., *Cancer Res.*, 47, 936–942, (1987)). The results are expressed as $IC_{50}$, the cytotoxic concentration that inhibits proliferation of treated cells by 50%. All the compounds of the invention exhibit good cytotoxicity towards this cell line. By way of example, in this test the compound of Example 13 has an $IC_{50}$ of 0.13 μM and the compound of Example 19 has an $IC_{50}$ of 0.14 μM.

Human Cell Lines

The compounds of the invention were also tested on human cell lines according to the same experimental protocol as that described for the murine leukaemia L1210, but for incubation periods of 4 days, instead of 2 days. By way of example, the compounds of Examples 14, 16, 19 and 29 all have an $IC_{50}$ of less than 1 μM on the following cell lines: ovarian carcinoma IGROV-1, neuroblastoma SK-N-MC, colon carcinoma HT-29, non-small cell pulmonary carcinoma A549, epidermoid carcinoma A431 and small-cell pulmonary carcinoma H 69.

These various results clearly show the considerable antitumour potential of the compounds of the invention.

EXAMPLE 42

Action on the Cell Cycle

The L1210 cells are incubated for 21 hours at 37° C. in the presence of various concentrations of test compounds. The cells are then fixed by 70% (v/v) ethanol, washed twice in PBS and incubated for 30 minutes at 20° C. in PBS that contains 100 μg/ml of RNAse and 50 μg/ml of propidium iodide. The results are expressed as a percentage of the cells that accumulate in the G2+M phase after 21 hours, compared with the control (control: 20%). The compounds of the invention are especially valuable. They induce an accumulation of at least 70% of cells in the G2+M phase after 21 hours at a concentration of less than 1 μM.

EXAMPLE 43

Pharmaceutical Composition: Injectable Solution

| Compound of Example 13 | 10 mg |
|---|---|
| Distilled water for injectable preparations | 25 ml |

What is claimed is:

1. A compound selected from those of formula (I):

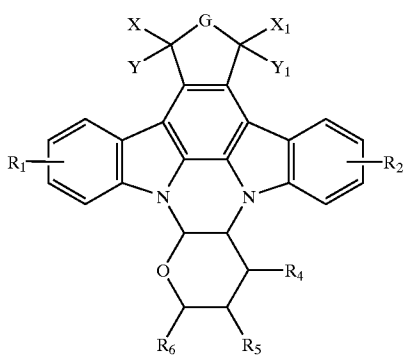

(I)

wherein:

$R_1$ and $R_2$, which may be identical or different, each independently of the other represents a group of formula U-V wherein:

U represents single bond, or linear or branched ($C_1$-$C_6$) alkylene which is optionally substituted by one or more, identical or different, groups selected from halogen, and hydroxy, and/or which contains optionally one or more unsaturated bonds, V represents a group selected from hydrogen, halogen, cyano, nitro, azido, linear or branched ($C_1$-$C_6$)alkyl, aryl, aryl-($C_1$-$C_6$)alkyl in which alkyl is linear or branched, hydroxy, linear or branched ($C_1$-$C_6$) alkoxy, aryloxy, aryl-($C_1$-$C_6$)-alkoxy in which alkoxy is linear or branched, formyl, carboxy, aminocarbonyl, NRaRb, —C(O)-$T_1$, —C(O)—NRa-$T_1$, —NRa—C(O)-$T_1$, —O—C(O)-$T_1$, —C(O)—O-$T_1$, —O-$T_2$-NRaRb, —O-$T_2$-ORa, —O-$T_2$-$CO_2$Ra, —NRa-$T_2$-NRaRb, —NRa-$T_2$—ORa, —NRa-$T_2$-$CO_2$Ra, and —S(O)$_n$—Ra, wherein:

Ra and Rb, which may be identical or different, each represents a group selected from hydrogen, linear or branched ($C_1$-$C_6$)alkyl, aryl, and aryl-($C_1$-$C_6$) alkyl in which alkyl is linear or branched, $T_1$ represents a group selected from linear or branched ($C_1$-$C_6$)alkyl, aryl, aryl ($C_1$-$C_6$)alkyl in which alkyl is linear or branched, and linear or branched ($C_1$-$C_6$)alkylene substituted by a group selected from —ORa, —NRaRb, —$CO_2$Ra, —C(O)Ra, and —C(O)NRaRb wherein Ra and Rb are as defined hereinbefore, $T_2$ represents linear or branched ($C_1$-$C_6$)alkylene, n represents an integer from 0 to 2 inclusive, G represents oxygen, or $NR_3$ wherein $R_3$ represents a group selected from hydrogen, linear or branched ($C_1$-$C_6$)alkyl, aryl, aryl-($C_1$-$C_6$)alkyl in which alkyl is linear or branched, cycloalkyl, cycloalkyl-($C_1$-$C_6$) alkyl in which alkyl is linear or branched, —ORa, —NRaRb, —O-$T_2$-NRaRb, —NRa-$T_2$-NRaRb, ($C_1$-$C_6$)hydroxyalkyl-amino in which alkyl is linear or branched, di(($C_1$-$C_6$)-hydroxyalkyl)amino in which each alkyl is linear or branched, —C(O)—Ra, —NH—C(O)—Ra, and linear or branched ($C_1$-$C_6$)alkylene substituted by one or more, identical or different, groups selected from halogen, cyano, nitro, —ORa, —NRaRb, —$CO_2$Ra, —C(O)Ra, ($C_1$-$C_6$) hydroxyalkylamino in which alkyl is linear or branched, di(($C_1$-$C_6$)hydroxyalkyl)amino in which each alkyl moiety is linear or branched, and —C(O)—NHRa, the groups Ra, Rb and $T_2$ being as defined hereinbefore, X represents a group selected from hydrogen, hydroxy, linear or branched ($C_1$-$C_6$)alkoxy, mercapto, and linear or branched ($C_1$-$C_6$)alkyl-thio, Y represents hydrogen, or X and Y, together with carbon carrying them, form carbonyl, $X_1$ represents a group selected from hydrogen, hydroxy, linear or branched ($C_1$-$C_6$)alkoxy, mercapto, and linear or branched ($C_1$-$C_6$)alkyl-thio, $Y_1$ represents hydrogen, or $X_1$ and $Y_1$, together with carbon carrying them, form carbonyl, $R_4$ and $R_5$, which may be identical or different, each independently of the other represents a group selected from hydrogen, halogen, hydroxy, linear or branched ($C_1$-$C_6$)alkoxy, aryloxy, aryl-($C_1$-$C_6$)alkoxy in which alkoxy is linear or branched, linear or branched ($C_1$-$C_6$)alkyl, aryl-($C_1$-$C_6$)alkyl in which alkyl is linear or branched, aryl, amino (itself being optionally substituted by one or two, identical or different, groups selected from linear or branched ($C_1$-$C_6$)alkyl, aryl, and aryl-($C_1$-$C_6$)alkyl in which alkyl is linear or branched), azido, —N═NRa (wherein Ra is as defined hereinbefore), and —O—C(O)-Rc wherein Rc represents linear or branched ($C_1$-$C_6$)alkyl (optionally substituted by one or more groups selected from halogen, hydroxy, amino, linear or branched ($C_1$-$C_6$) alkylamino, and di-($C_1$-$C_6$)alkyl-amino in which each alkyl moiety is linear or branched), aryl, aryl-($C_1$-$C_6$)-alkyl in which alkyl is linear or branched, and cycloalkyl, $R_6$ represents a group of formula —$U_1$-$R_4$ wherein $U_1$ represents single bond, or methylene, and $R_4$ is as defined hereinbefore, or $R_4$, $R_5$, and $R_6$ taken in pairs in adjacent or non-adjacent positions form with carbon carrying them a ring having from 3 to 6 ring members, having one, or two oxygen, with the remaining group $R_4$, $R_5$ or $R_6$ that does not belong to the ring having any one of the definitions of $R_4$, $R_5$, or $R_6$ given hereinbefore, its optical isomers, and pharmaceutically-acceptable acid or base addition salts thereof, provided that the compound of formula (I) is other than the following compounds:

1,11-dichloro-12,13-[1,2-(4-O-methyl-β-D-mannopyranosyl)]-6,7,12,13-tetrahydro-(5H)-indolo[2,3-a]pyrrolo[3,4-c]carbazole-5,7-dione, 12,13-[1,2-(4-O-methyl-β-D-mannopyranosyl)-6,7,12,13-tetrahydro-(5H)-indolol[2,3-a]-pyrrolo[3,4-c]carbazole-5,7-dione, 12,13-[1,2-(4-O-methyl-β-D-mannopyranosyl)-6,7,12,13-tetrahydro-(5H-indolo[2,3-a]-pyrrolo[3,4-c]carbazol-5-one, and 12,13-[1,2-(4-O-methyl-β-D-mannopyranosyl)-5,6,12,13-tetrahydro-(7H-indolo[2,3-a]-pyrrolo[3,4-c]-carbazol-7-one, it also being understood that:

"cycloalkyl" is understood to mean monocyclic or bicyclic, that is saturated or unsaturated, but without aromatic character, having from 3 to 10 carbon, being optionally substituted by one or more, identical or different, groups selected from halogen, linear or branched ($C_1$–$C_6$)alkyl, linear or branched ($C_1$–$C_6$)trihaloalkyl, hydroxy, linear or branched ($C_1$–$C_6$)alkoxy, and amino optionally substituted by one or two linear or branched ($C_1$–$C_6$)alkyl groups, "aryl" is understood to mean phenyl, naphthyl, dihydronaphthyl, tetrahydronaphthyl, indenyl, or indanyl, each of those groups being optionally substituted by one or more, identical or different, groups selected from halogen, linear or branched ($C_1$–$C_6$)-alkyl, linear or branched ($C_1$–$C_6$)trihaloalkyl, hydroxy, linear or branched ($C_1$–$C_6$)-alkoxy, and amino optionally substituted by one or two, linear or branched ($C_1$–$C_6$)alkyl.

2. A compound of claim 1 wherein G represents $NR_3$.

3. A compound of claim 1 wherein X and Y, together with the carbon carrying them, form carbonyl, and $X_1$ and $Y_1$, together with the carbon carrying them, form carbonyl.

4. A compound of claim 1 having the formula (Ibis):

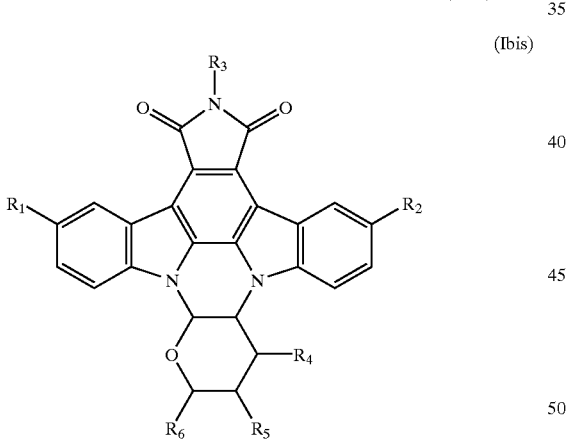

(Ibis)

wherein $R_1$, $R_2$, $R_3$, $R_4$, $R_5$, and $R_6$ are as defined in claim 1.

5. A compound of claim 1, wherein $R_1$ and $R_2$, which may be identical or different, represent a group of formula U-V wherein U represents a single bond and V represents a group selected from halogen, hydrogen, nitro, formyl, hydroxy, and linear or branched ($C_1$–$C_6$)alkylene substituted by hydroxy.

6. A compound of claim 1 wherein $R_1$ and $R_2$ are identical.

7. A compound of claim 1 wherein $R_3$ represents hydrogen, hydroxy or linear or branched ($C_1$–$C_6$)alkylene substituted by a group selected from NRaRb and ORa.

8. A compound of claim 1 having the formula (Iter):

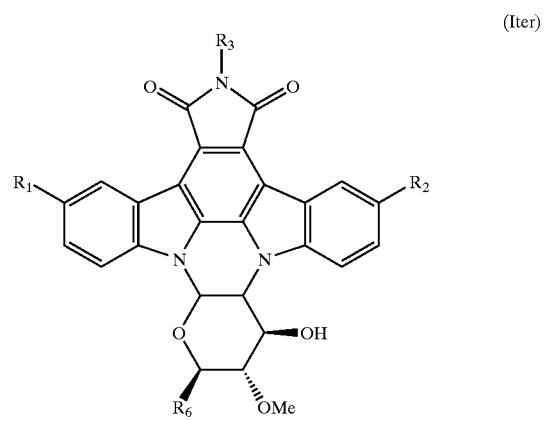

(Iter)

wherein $R_1$, $R_2$, $R_3$ and $R_6$ are as defined in formula (I).

9. A compound of claim 1 selected from:

3,9-diformyl-12,13-[1,2-(4-O-methyl-β-D-mannopyranosyl)]-6,7,12,13-tetrahydro-(5H)-indolo [2,3-a]pyrrolo[3,4-c]carbazole-5,7-dione, 3,9-dinitro-12,13-[1,2-(4-O-methyl-β-D-mannopyranosyl)]-6,7,12,13-tetrahydro-(5H)-indolo [2,3-a]pyrrolo[3,4-c]carbazole-5,7-dione, 3-nitro-12,13-[1,2-(4-O-methyl-β-D-mannopyranosyl)]-6,7,12,13-tetrahydro-(5H)-indolo [2,3-a]pyrrolo[3,4-c] carbazole-5,7-dione, 9-nitro-12,13-[1,2-(4-O-methyl-β-D-mannopyranosyl)]-6,7,12,13-tetrahydro-(5H)-indolo[2,3-a]pyrrolo[3,4-c] carbazole-5,7-dione, 6-hydroxy-12,13-[1,2-(4-O-methyl-β-D-mannopyranosyl)]-6,7,12,13-tetrahydro-(5H)-indolo [2,3-a]pyrrolo[3,4-c]carbazole-5,7-dione, 3,9-di-(hydroxymethyl)-12,13-[1,2-(4-O-methyl-β-D-mannopyranosyl)]-6,7,12,13-tetrahydro-(5H)-indolo [2,3-a]pyrrolo[3,4-c]carbazole-5,7-dione, 3,9-dinitro-12,13-[1,2-(3,6-anhydro-4-O-methyl-β-D-mannopyranosyl)]-6,7,12,13-tetrahydro-(5H-indolo[2,3-a]pyrrolo [3,4-c]carbazole-5,7-dione, 3,9-dihydroxy-12,13-[1,2-(4-O-methyl-β-D-mannopyranosyl)]-6,7,12,13-tetrahydro-(5H-indolo[2,3-a]pyrrolo[3,4-c]carbazole-5,7-dione, 3,9-dibromo-12,13-[1,2-(4-O-methyl-β-D-mannopyranosyl)]-6,7,12,13-tetrahydro-(5H)-indolo [2,3-a]pyrrolo[3,4-c]carbazole-5,7-dione, and 6-diethylaminoethyl-12,13-[1,2-(4-O-methyl-β-D-mannopyranosyl)]-6,7,12,13-tetrahydro-(5H)-indolo [2,3-α]pyrrolo[3,4-c]carbazole-5,7-dione and its hydrochloride. its isomers, and pharmaceutically-acceptable acid or base addition salts thereof.

10. A method for treating a living body afflicted with cancer, selected from leukaemia, ovarian cancer, neuroblastoma, colon cancer, non-small cell pulmonary cancer, epidermoid carcinoma, and small cell pulmonary carcinoma, comprising the step of administering to the living body an amount of a compound of claim 1, which is effective for alleviation of said cancer.

11. A pharmaceutical composition for treating cancer, selected from leukaemia, ovarian cancer, neuroblastoma, colon cancer, non-small cell pulmonary cancer, epidermoid carcinoma, and small cell pulmonary carcinoma, comprising as active principle an effective amount of a compound as claimed in claim 1, together with one or more pharmaceutically-acceptable excipients of vehicles.

* * * * *

UNITED STATES PATENT AND TRADEMARK OFFICE
CERTIFICATE OF CORRECTION

PATENT NO.     : 6,569,858 B2
DATED          : May 27, 2003
INVENTOR(S)    : Michelle Prudhomme et al.

It is certified that error appears in the above-identified patent and that said Letters Patent is hereby corrected as shown below:

<u>Column 23,</u>
Line 5, "(7H-indolo" should be -- (7H)-indolo --.

Signed and Sealed this

Fifth Day of August, 2003

JAMES E. ROGAN
*Director of the United States Patent and Trademark Office*